(12) United States Patent
Schröder et al.

(10) Patent No.: US 8,436,142 B2
(45) Date of Patent: May 7, 2013

(54) PROCESSING OF RECOMBINANT HUMAN G-CSF PRECURSOR

(75) Inventors: Carola Schröder, Neuried (DE); Elisabeth Casademunt, Munich (DE); Peter Söhlemann, Neubiberg (DE); Michael Lehnerer, Munich (DE)

(73) Assignee: Octapharma AG, Lachen (CH)

( * ) Notice: Subject to any disclaimer, the term of this patent is extended or adjusted under 35 U.S.C. 154(b) by 0 days.

(21) Appl. No.: 13/122,487

(22) PCT Filed: Oct. 2, 2009

(86) PCT No.: PCT/EP2009/062843
§ 371 (c)(1),
(2), (4) Date: May 19, 2011

(87) PCT Pub. No.: WO2010/037855
PCT Pub. Date: Apr. 8, 2010

(65) Prior Publication Data
US 2011/0294989 A1    Dec. 1, 2011

(30) Foreign Application Priority Data
Oct. 2, 2008   (EP) .................................. 08165758

(51) Int. Cl.
*A61K 38/00* (2006.01)
*C07H 21/04* (2006.01)
*C12N 15/00* (2006.01)

(52) U.S. Cl.
USPC ...... 530/350; 536/23.5; 435/69.1; 435/320.1; 435/325

(58) Field of Classification Search ................... None
See application file for complete search history.

(56) References Cited

FOREIGN PATENT DOCUMENTS
EP    0215126 A1   3/1987
WO    WO-01/51510 A2   7/2001

OTHER PUBLICATIONS

Chinese Office Action dated Feb. 8, 2013, issued in corresponding Chinese Patent Application No. 20980137913.5.
"Signal Peptidases", Mark Paetzel, et al., Chemical Review, 102(12), pp. 4549-4579, Aug. 11, 2002.

*Primary Examiner* — Gyan Chandra
(74) *Attorney, Agent, or Firm* — Venable LLP; Nancy J. Axelrod; Michael A. Gollin

(57) ABSTRACT

A G-CSF precursor comprising a signal peptide and a G-CSF peptide, wherein the signal peptide has the sequence of the human wild-type signal peptide of the human G-CSF/b molecule with at least one of the following mutations:
deletion of Glu29,
insertion of Glu26,
substitution Lys11Leu,
substitution His21Phe, and
substitution Gln28Leu.

20 Claims, 19 Drawing Sheets

G-CSF (SP9 signal peptide) – residue 5

|   | Main sequence | Minor sequences |
|---|---|---|
| 1 | T |  |
| 2 | P | DLY |
| 3 | L | AQ |
| 4 | G | QK |
| 5 | P | DQ |

G-CSF (SP10 signal peptide) – residue 5

| | Main sequence | Minor sequences |
|---|---|---|
| 1 | T | |
| 2 | P | DLY |
| 3 | L | GAQ |
| 4 | G | QK |
| 5 | P | DQA |

|   | Main sequence | Minor sequences |
|---|---|---|
| 1 | T | |
| 2 | P | |
| 3 | L | |
| 4 | G | |
| 5 | P | |

| | Main sequence | Minor sequences |
|---|---|---|
| 1 | T | G |
| 2 | P | P    DL |
| 3 | L | A |
| 4 | G | S    Q |
| 5 | P | S    DQ |

SEQUENCE LISTING

```
<160> NUMBER OF SEQ ID NOS: 7

<210> SEQ ID NO 1
<211> LENGTH: 204
<212> TYPE: PRT
<213> ORGANISM: Homo sapiens

<400> SEQUENCE: 1

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200

<210> SEQ ID NO 2
<211> LENGTH: 204
<212> TYPE: PRT
<213> ORGANISM: Homo sapiens

<400> SEQUENCE: 2

Met Ala Gly Pro Ala Thr Gln Ser Pro Met Lys Leu Met Ala Leu Gln
1               5                   10                  15

Leu Leu Leu Trp His Ser Ala Leu Trp Glu Thr Val Gln Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
```

```
                50                  55                  60
Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                     85                  90                  95

Gln Ala Leu Gln Leu Ala Gly Cys Leu Ser Gln Leu His Ser Gly Leu
                100                 105                 110

Phe Leu Tyr Gln Gly Leu Leu Gln Ala Leu Glu Gly Ile Ser Pro Glu
                115                 120                 125

Leu Gly Pro Thr Leu Asp Thr Leu Gln Leu Asp Val Ala Asp Phe Ala
                130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
                180                 185                 190

Val Ser Tyr Arg Val Leu Arg His Leu Ala Gln Pro
                195                 200
```

<210> SEQ ID NO 3
<211> LENGTH: 204
<212> TYPE: PRT
<213> ORGANISM: Homo sapiens

<400> SEQUENCE: 3

```
Met Ala Gly Pro Ala Thr Gln Ser Pro Met Leu Leu Met Ala Leu Gln
 1               5                  10                  15

Leu Leu Leu Trp Phe Ser Ala Leu Trp Thr Val Leu Glu Ala Thr Pro
                 20                  25                  30

Leu Gly Pro Ala Ser Ser Leu Pro Gln Ser Phe Leu Leu Lys Cys Leu
                 35                  40                  45

Glu Gln Val Arg Lys Ile Gln Gly Asp Gly Ala Ala Leu Gln Glu Lys
                 50                  55                  60

Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                     85                  90                  95

Gln Ala Leu Gln Leu Ala Gly Cys Leu Ser Gln Leu His Ser Gly Leu
                100                 105                 110

Phe Leu Tyr Gln Gly Leu Leu Gln Ala Leu Glu Gly Ile Ser Pro Glu
                115                 120                 125

Leu Gly Pro Thr Leu Asp Thr Leu Gln Leu Asp Val Ala Asp Phe Ala
                130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
                180                 185                 190

Val Ser Tyr Arg Val Leu Arg His Leu Ala Gln Pro
                195                 200
```

<210> SEQ ID NO 4
<211> LENGTH: 30
<212> TYPE: PRT

```
<213> ORGANISM: Homo sapiens

<400> SEQUENCE: 4

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala
            20                  25                  30

<210> SEQ ID NO 5
<211> LENGTH: 40
<212> TYPE: PRT
<213> ORGANISM: homo sapiens

<400> SEQUENCE: 5

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro
        35                  40

<210> SEQ ID NO 6
<211> LENGTH: 40
<212> TYPE: PRT
<213> ORGANISM: homo sapiens

<400> SEQUENCE: 6

Met Ala Gly Pro Ala Thr Gln Ser Pro Met Lys Leu Met Ala Leu Gln
1               5                   10                  15

Leu Leu Leu Trp His Ser Ala Leu Trp Glu Thr Val Gln Ala Thr Pro
            20                  25                  30

Leu Gly Pro Ala Ser Ser Leu Pro
        35                  40

<210> SEQ ID NO 7
<211> LENGTH: 40
<212> TYPE: PRT
<213> ORGANISM: homo sapiens

<400> SEQUENCE: 7

Met Ala Gly Pro Ala Thr Gln Ser Pro Met Leu Leu Met Ala Leu Gln
1               5                   10                  15

Leu Leu Leu Trp Phe Ser Ala Leu Trp Thr Val Leu Glu Ala Thr Pro
            20                  25                  30

Leu Gly Pro Ala Ser Ser Leu Pro
        35                  40
```

PROCESSING OF RECOMBINANT HUMAN G-CSF PRECURSOR

This application is a National Stage Application of International Application No. PCT/EP2009/062843, filed Oct. 2, 2009, which claims priority to European Patent Application No. 08165758.7, filed Oct. 2, 2008, the entire contents of which are hereby incorporated by reference in their entirety.

BACKGROUND OF THE INVENTION

G-CSF is a 20 kDa glycoprotein stabilized by two intrachain disulfide bonds and containing a single O-linked carbohydrate moiety. Mature G-CSF has 174 amino acids. G-CSF is synthesized by bone marrow cells, macrophages and fibroblasts. Its main function is to be a growth and differentiation factor for neutrophilic granulocytes and their precursor cells. It is also known in the art that G-CSF activates mature neutrophils. In addition, it stimulates growth/differentiation of various other haemopoietic progenitor cells (in synergy with additional haemopoietic growth factors) and promotes proliferation and migration of endothelial cells. Clinically, G-CSF is used for the treatment of deficiencies in neutrophilic granulocyte levels (neutropenia caused, e.g. by cancer/chemotherapy, AIDS, or bone marrow transplantation).

SUMMARY OF THE INVENTION

In order to treat neutropenia patients with human identical G-CSF, human cells were transfected with a plasmid encoding human wild-type G-CSF. After purification of G-CSF from cell culture supernatant of selected clones, it was observed that a substantial amount of secreted G-CSF was N-terminally truncated by three amino acids. This truncation was not clone specific and could not be eliminated by modification of cell culture conditions.

On the basis of this observation it was concluded that processing of the G-CSF precursor protein in cells, especially HEK293F cells was not precise. In detail, it was concluded that the signal peptidase complex did not only cleave at the expected position in order to physiologically remove the signal peptide, but additionally at one more position leading to the N-terminal truncation.

DETAILED DESCRIPTION OF THE INVENTION

Surprisingly it has been found that N-terminal truncation can be reduced if a modified signal peptide and a corresponding G-CSF precursor is used.

Therefore, in one embodiment the invention provides a G-CSF precursor comprising a signal peptide and a G-CSF peptide, wherein the signal peptide has the sequence of the human wild-type signal peptide of the human G-CSF/b molecule (SEQ ID NO: 4) with at least one of the following mutations:
  deletion of Glu29,
  insertion of Glu26,
  substitution Lys11Leu,
  substitution His21Phe, and
  substitution Gln28Leu.

In a preferred embodiment, the G-CSF precursor has at least 2 or at least 3 or at least 4 or all five mutations mentioned above.

In a further embodiment of the invention, the G-CSF precursor has up to 3 additional mutations selected from insertion, deletion and substitution.

A further embodiment of the invention is a polynucleotide coding for the G-CSF precursor of the invention and a polynucleotide complementary to the above-mentioned polynucleotide.

A further embodiment of the invention is a vector comprising the polynucleotide of the invention and a transfected cell comprising either the polynucleotide of the invention or the vector of the invention.

In a preferred embodiment it is an eukaryotic cell, preferably a human cell, more preferably a HEK293 cell and more preferably a HEK293F or a HEK293F derived cell.

In one embodiment the transfection is transient and in an other embodiment the transfection is stable.

A further embodiment of the invention is a method for expressing G-CSF comprising the steps of
  culturing transfected cells of the invention in a suitable culture medium
  isolating G-CSF from the culture medium.

In a preferred embodiment, the culturing is at a pH within the range of 6.8 to 7.5, preferably 7.1 to 7.3, more preferably around 7.2. Preferably the pH is controlled during culturing.

In a further embodiment, the culturing is in the presence of insulin in the range of 5 to 25 mg/ml, preferably 15 to 25 mg/ml, more preferably 15 to 20 mg/ml.

Surprisingly with the modified signal peptide of the invention the produced G-CSF has a very small truncation ratio, preferably below 5% of molecules, more preferably below 1% of the total G-CSF. 1% is considered to be the detection limit.

Preferably, the cultivation medium is serum-free.

The glycosylation pattern of the major G-CSF is unchanged and the activity is the same as wild-typed G-CSF.

Therefore, the method of the present invention produces a G-CSF which is highly suitable for pharmaceutical applications.

DESCRIPTION OF THE FIGURES

FIGS. 5a to 5e correspond to residues 1 to 5. A summary of the amino acid sequence analysis is given in the table below.

FIGS. 6a to 6e correspond to residues 1 to 5. A summary of the amino acid sequence analysis is given in the table below.

FIGS. 7a to 7e correspond to residues 1 to 5. A summary of the amino acid sequence analysis is given in the table below.

FIGS. 8a to 8e correspond to residues 1 to 5). A summary of the amino acid sequence analysis is given in the table below.

EXAMPLE 1

Optimization of the G-CSF precursor peptide for correct protein processing

The wild-type, human G-CSF isoform b cDNA was published in the GenBank database (NM_172219). Essentially any G-CSF precursor protein having any sequence derived from NM_172219 is of use for the modification of signal peptide sequence of the present invention. In an exemplary embodiment, the precursor protein has the sequence presented herein as SEQ ID NO: 1 (GenBank NP_757373):

MAGPATQSPMKLMALQLLLWHSALWTVQEATPLGPASSLPQSFLLKCLEQV

RKIQGDGAALQEKLCATYKLCHPEELVLLGHSLGIPWAPLSSCPSQALQLA

GCLSQLHSGLFLYQGLLQALEGISPELGPTLDTLQLDVADFATTIWQQMEE

LGMAPALQPTQGAMPAFASAFQRRAGGVLVASHLQSFLEVSYRVLRHLAQP

The unprocessed wild-type G-CSF precursor protein (SEQ ID NO: 1) comprises 204 amino acids including a signal peptide of 30 amino acids. Processing is published to occur between residues Ala30 and Thr31 (GenBank NP_757373).

Recent literature describes the eukaryotic signal peptide consensus sequence and the function of the signal peptidase complex (Rapoport, 2007, Nature 450 (29), 663-669; Tuteja, 2005, Arch Biochem Biophys 441, 107-111; Dalbey et al., 1997, Protein Science 6, 1129-1138).

The amino acid sequence of G-CSF signal peptide was compared with the proposed features of the consensus signal peptide described above. It was found that several amino acid residues do not fit to the proposed model. In detail, the proposed Ala-X-Ala motif at the C-terminal end of the signal peptide, which is considered to be crucial for the precision of cleavage, is interrupted by a charged amino acid (Glu29) in the G-CSF precursor peptide. Moreover, the charged residues Lys11 and His21 are located in the hydrophobic region of the signal peptide and thus are not in line with the requirements of the model.

Figure 1:
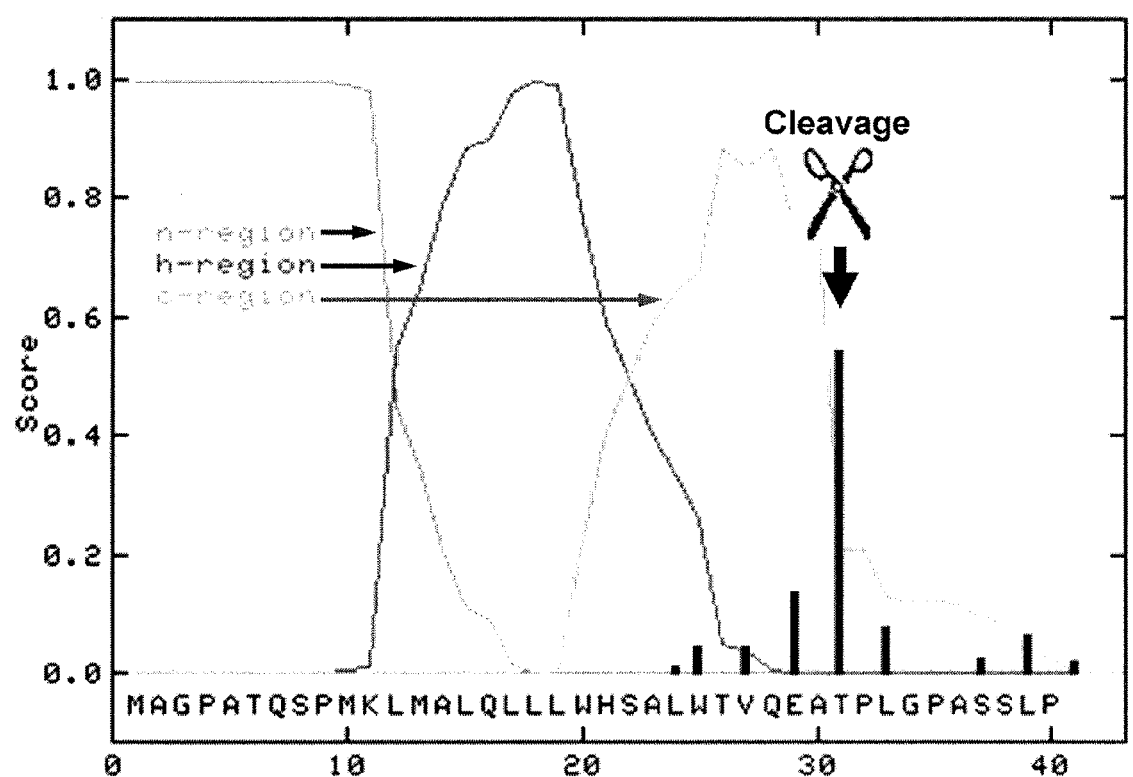
FIG. 1 shows the analysis of human, wild-type G-CSF with wild-type signal peptide using the Program TargetP. "The peptide shown in the figure is represented by SEQ ID NO:5."

The wild-type G-CSF signal peptide was analyzed in silico with the software SignalP and TargetP (the world wide web page cbs.dtu.dk/services; Emanuelsson et al., 2007, Nature Protocols 2, 953-971). The software showed that processing is predicted at the correct G-CSF N-terminus (Thr31), but additionally at several other sites (FIG. 1). Processing at the site of truncation (Gly34), however, was not predicted by this software.

EXAMPLE 2

Figure 2:
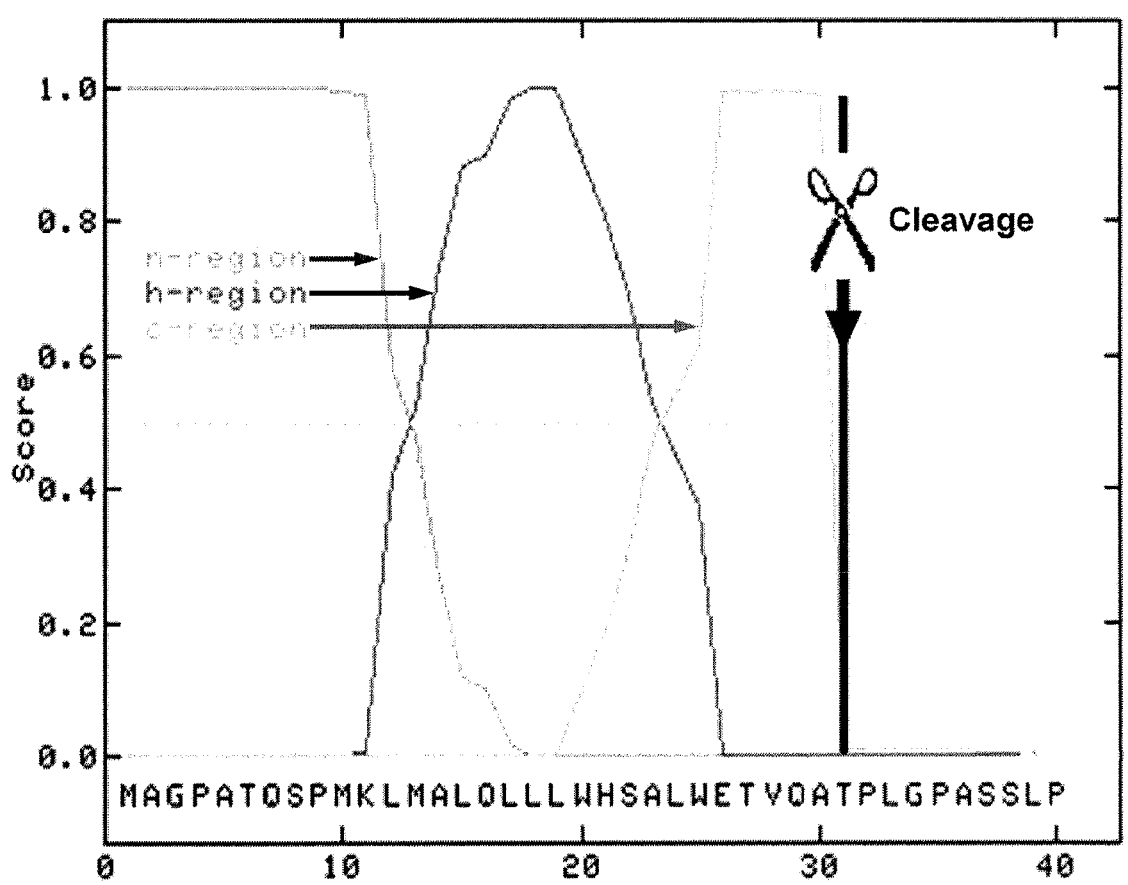
FIG. 2 shows the analysis of human, wild-type G-CSF with the SP9 signal peptide using the progam TargetP. "The peptide shown in the figure is represented by SEQ ID NO:6."
Figure 3:
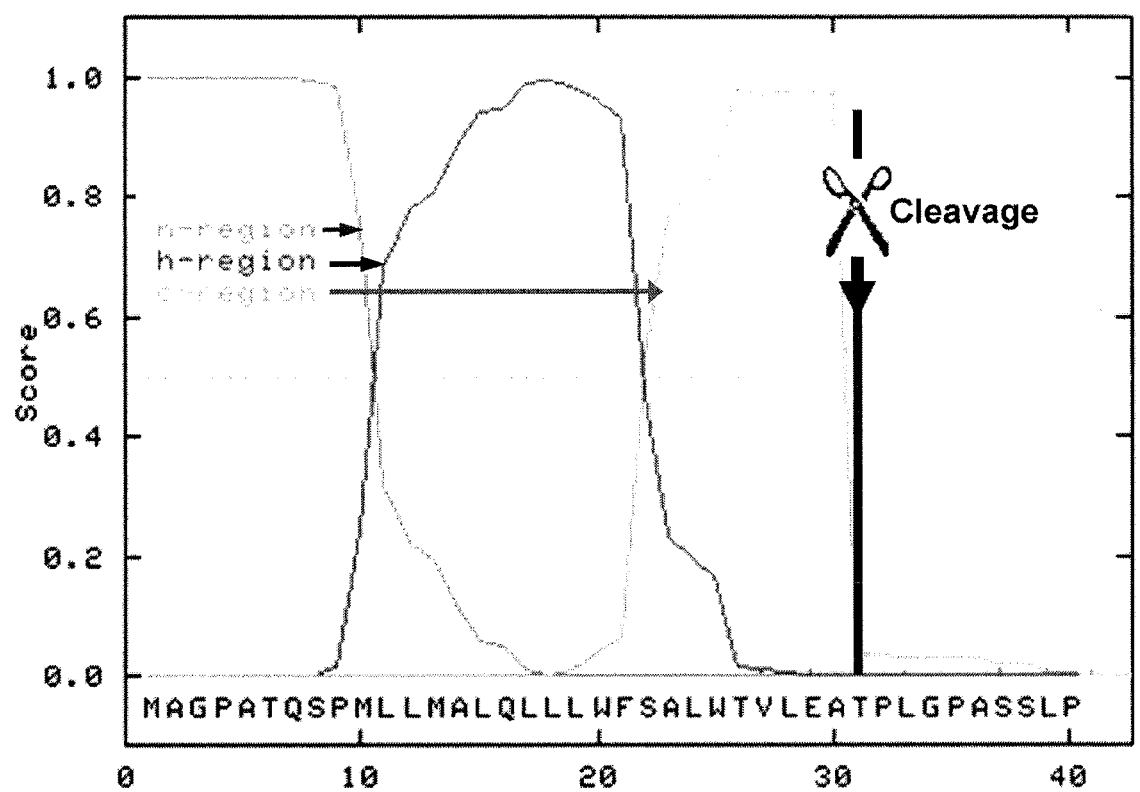
FIG. 3 shows the analysis of human, wild-type G-CSF with SP10 signal peptide using the program TargetP. "The peptide shown in the figure is represented by SEQ ID NO:7."

The wild-type G-CSF signal peptide was modelled in silico by minimal changes in its amino acid sequence with respect to the hypothetical signal peptidase model indicated above. The resulting cleavage position was again analyzed using the software SignalP and TargetP. Few in silico designed models, e.g. named as SP9 G-CSF and SP10 G-CSF, resulted in prediction of only the correct position (Thr31) for G-CSF processing, which was taken as a hint for an optimized signal peptide (see FIG. 2 and FIG. 3 for in silico analysis of SP9 G-CSF and SP10 G-CSF cleavage sites, respectively). Several such constructs were selected for gene synthesis (GeneArt, Regensburg, Germany). The synthetic genes coding for SP9 G-CSF and SP10 G-CSF peptides, respectively, were cloned into an eukaryotic expression vector and used for transfection of HEK293F cells.

EXAMPLE 3

SP9 G-CSF Precursor Protein

The SP9 G-CSF precursor protein results from the signal peptide sequence of the wild-type, human G-CSF precursor protein (SEQ ID NO: 1). In detail, glutamic acid at position 29 (Glu29) of the wild-type signal peptide was removed and inserted at position 26 (Glu26). In an exemplary embodiment, the SP9 G-CSF precursor protein has the sequence presented herein as SEQ ID NO: 2:

```
MAGPATQSPMKLMALQLLLWHSALWETVQATPLGPASSLPQSFLLKCLEQV
RKIQGDGAALQEKLCATYKLCHPEELVLLGHSLGIPWAPLSSCPSQALQLA
GCLSQLHSGLFLYQGLLQALEGISPELGPTLDTLQLDVADFATTIWQQMEE
LGMAPALQPTQGAMPAFASAFQRRAGGVLVASHLQSFLEVSYRVLRHLAQP
```

EXAMPLE 4

SP10 G-CSF Precursor Protein

The SP10 G-CSF precursor protein results from the signal peptide sequence of wild-type, human G-CSF (SEQ ID NO: 1). In detail, by substituting lysine at position 11 for leucine (Lys11Leu), histidine 21 for phenyl alanine (His21Phe) and glutamine 28 for leucine (Gln28Leu). In an exemplary embodiment, the SP10 G-CSF peptide has the sequence presented herein as SEQ ID NO: 3:

```
MAGPATQSPMLLMALQLLLWFSALWTVLEATPLGPASSLPQSFLLKCLEQV
RKIQGDGAALQEKLCATYKLCHPEELVLLGHSLGIPWAPLSSCPSQALQLA
GCLSQLHSGLFLYQGLLQALEGISPELGPTLDTLQLDVADFATTIWQQMEE
LGMAPALQPTQGAMPAFASAFQRRAGGVLVASHLQSFLEVSYRVLRHLAQP
```

It is important to note that despite the changes made in the signal peptide, the mature G-CSF peptide remains wild-type (SEQ ID NO: 1, SEQ ID NO: 2, SEQ ID NO: 3, residues 31-204).

EXAMPLE 5

Figure 4:
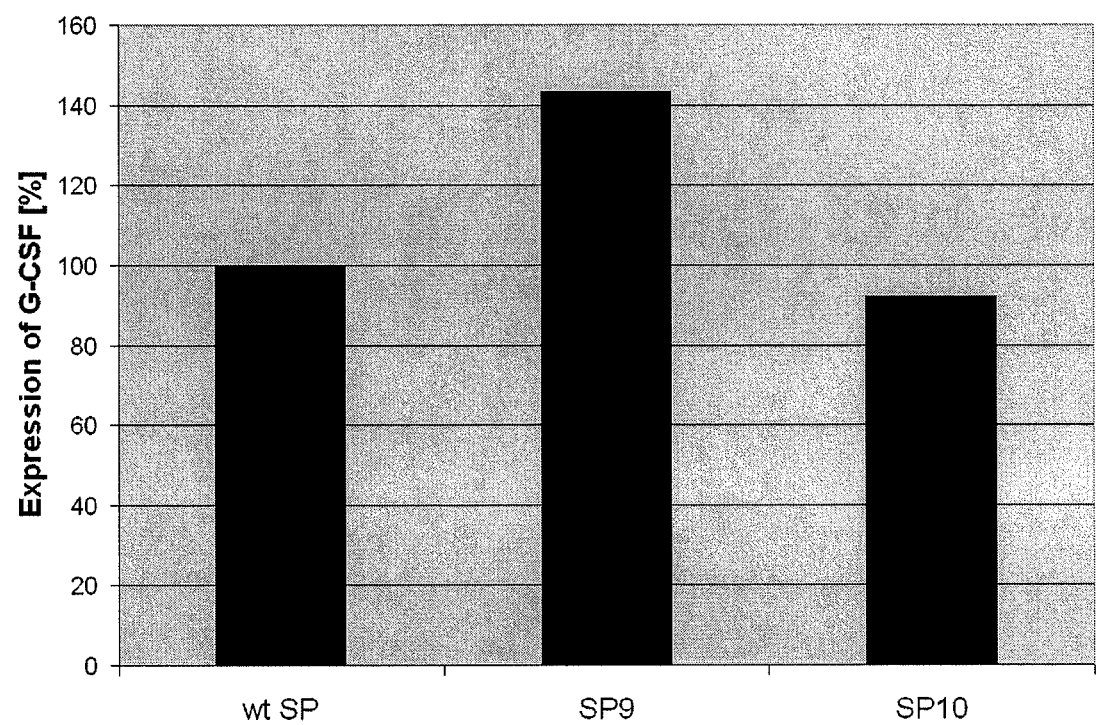
FIG. 4 shows the expression of mature G-CSF protein in HEK293F cells using constructs coding for precursor proteins with wild-type signal peptide (expression level is 100%), with SP9 or SP10 signal peptides, respectively.

Transient Transfections with Expression Vectors Coding for SP9 G-CSF and SP10 G-CSF HEK293F cells were transiently transfected with expression vectors coding for SP9 G-CSF, or SP10 G-CSF, respectively. Supernatants were collected after three days. G-CSF secretion was measured by ELISA. Data showed expression levels comparable to G-CSF with wild-type signal peptide or even a higher expression level (FIG. 4).

G-CSF was purified to high purity. Purification of the two products, SP9 G-CSF and SP10 G-CSF, respectively, was performed like wild-type G-CSF without any modification of the protocol.

EXAMPLE 6

Figure 5:
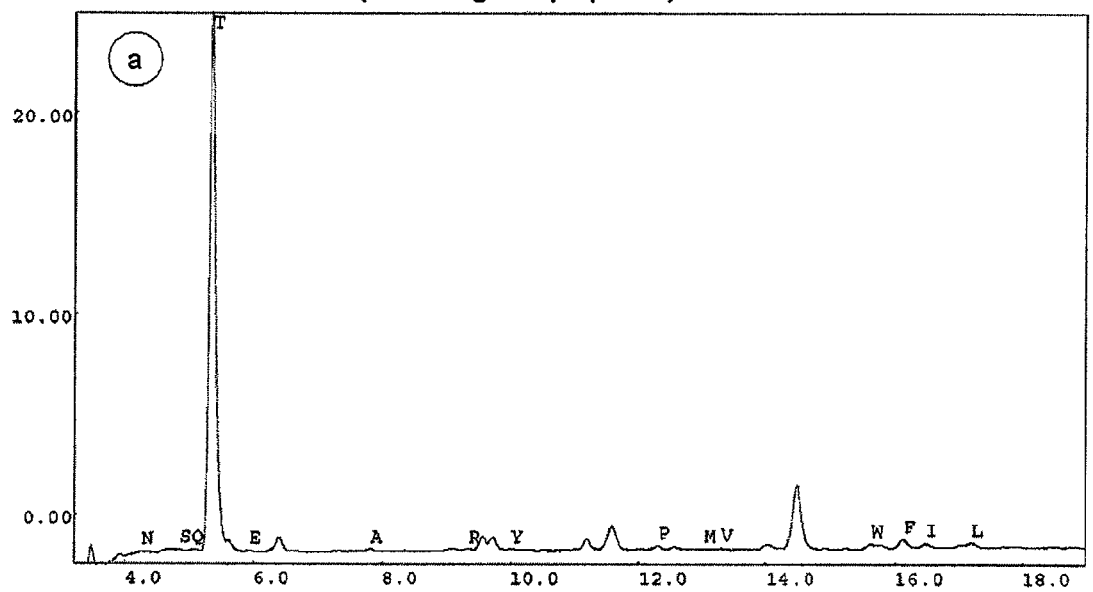
FIG. 5 shows the chromatogram of amino terminal amino acid sequencing (Edman degradation) of human, wild-type G-CSF with SP9 signal peptide.
Figure 5:
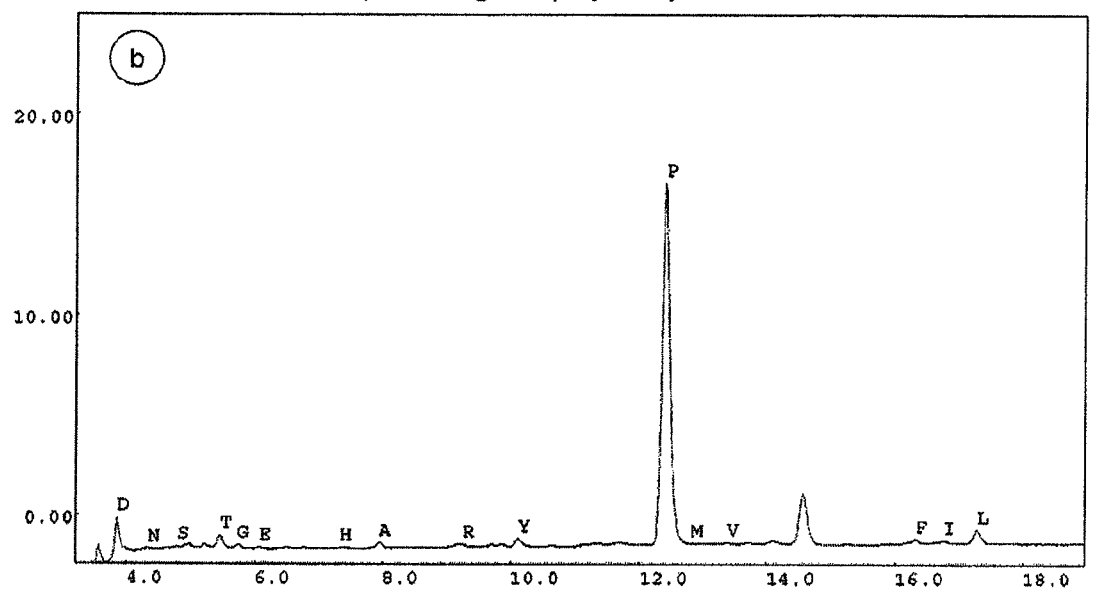
Figure 5:
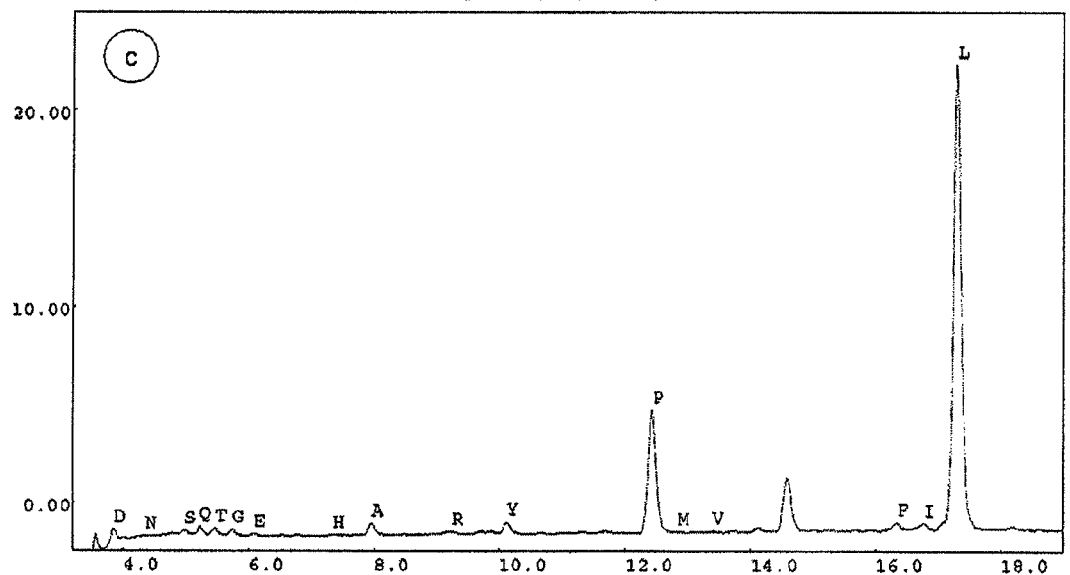
Figure 5:
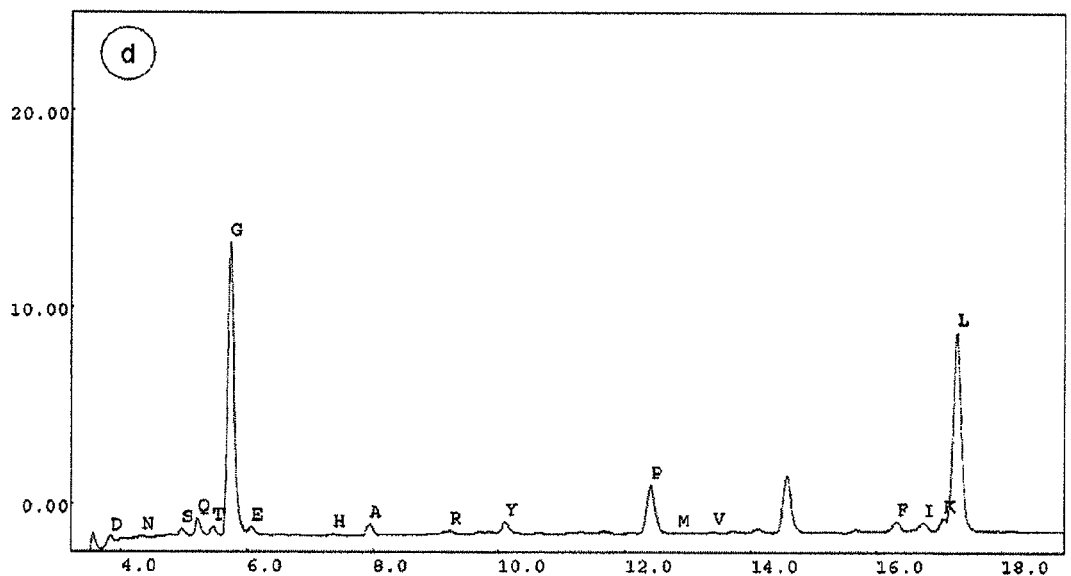
Figure 5:
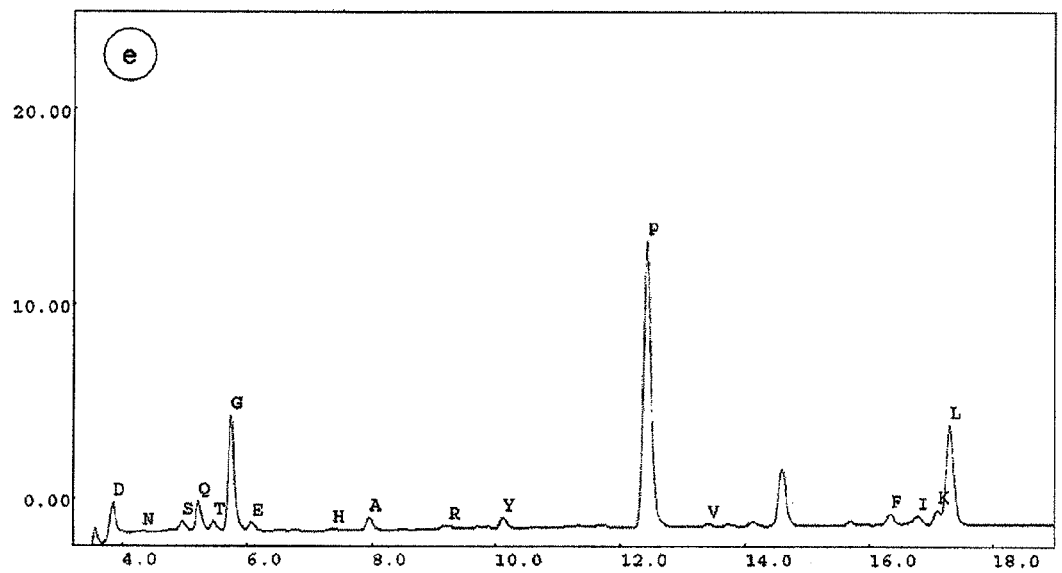
Figure 6:
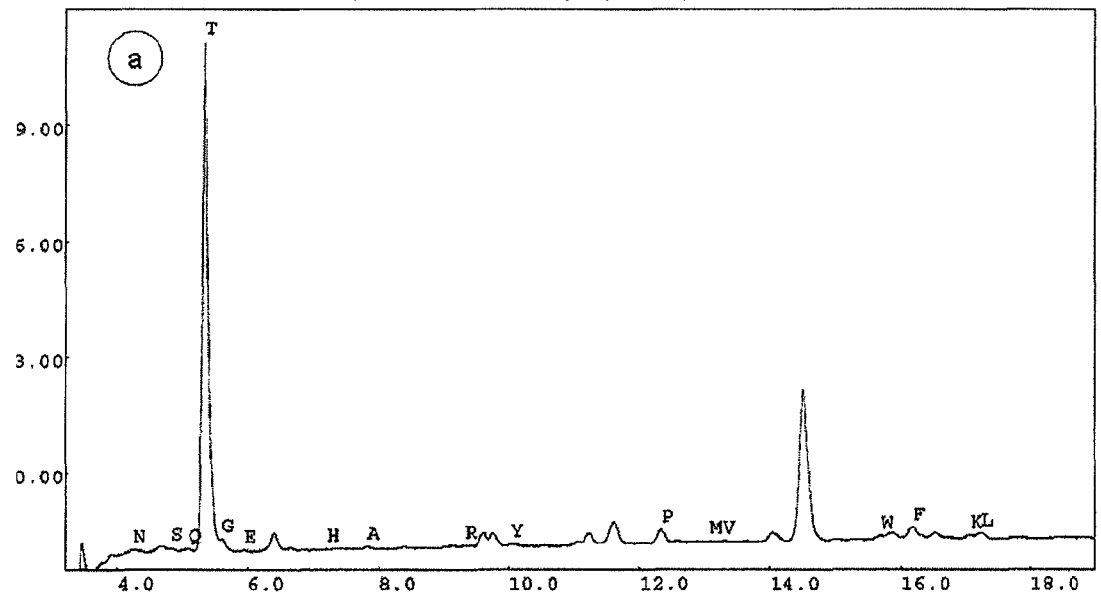
FIG. 6 shows the chromatogram of amino terminal amino acid sequencing (Edman degradation) of human, wild-type G-CSF with SP10 signal peptide.
Figure 6:
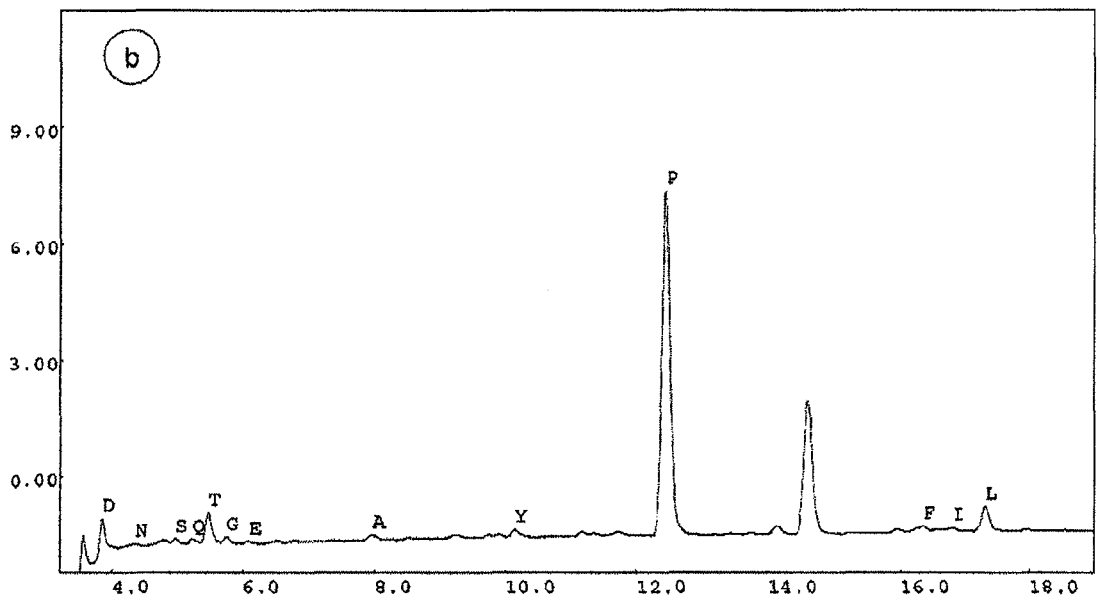
Figure 6:
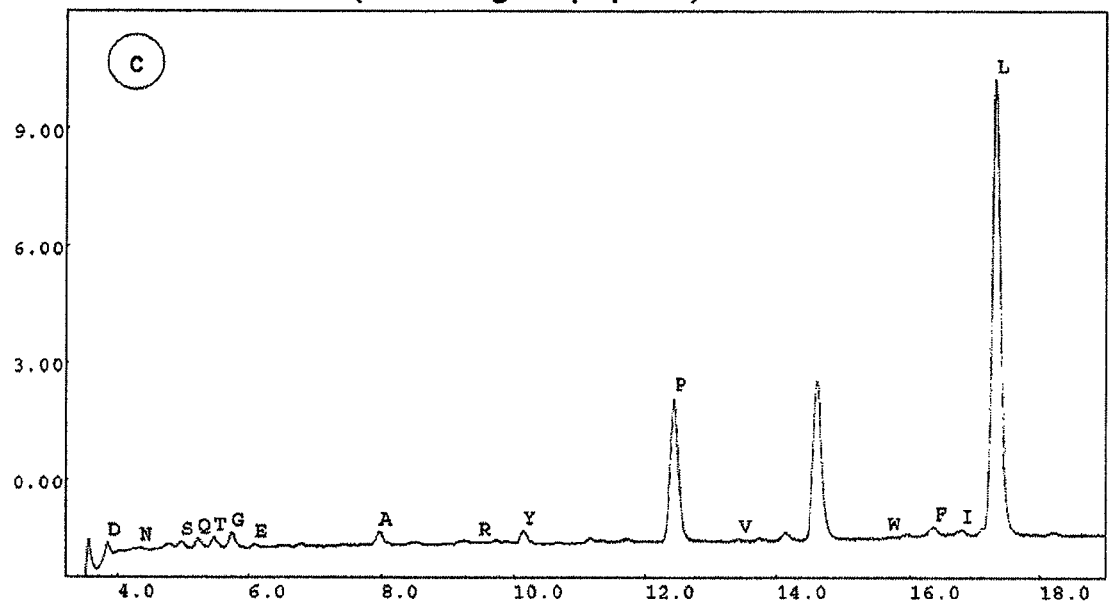
Figure 6:
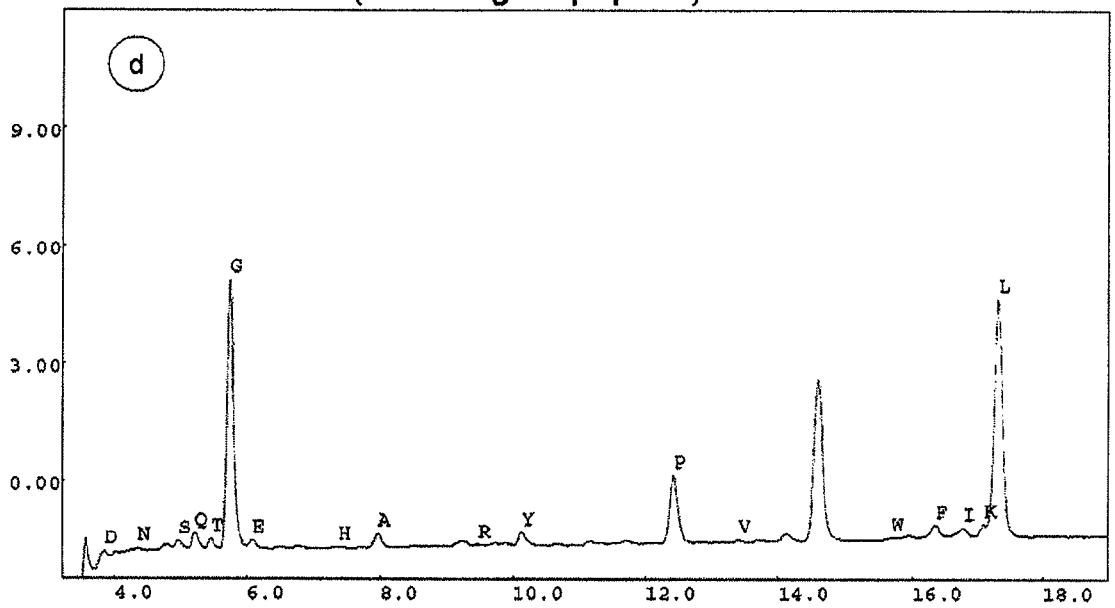
Figure 6:
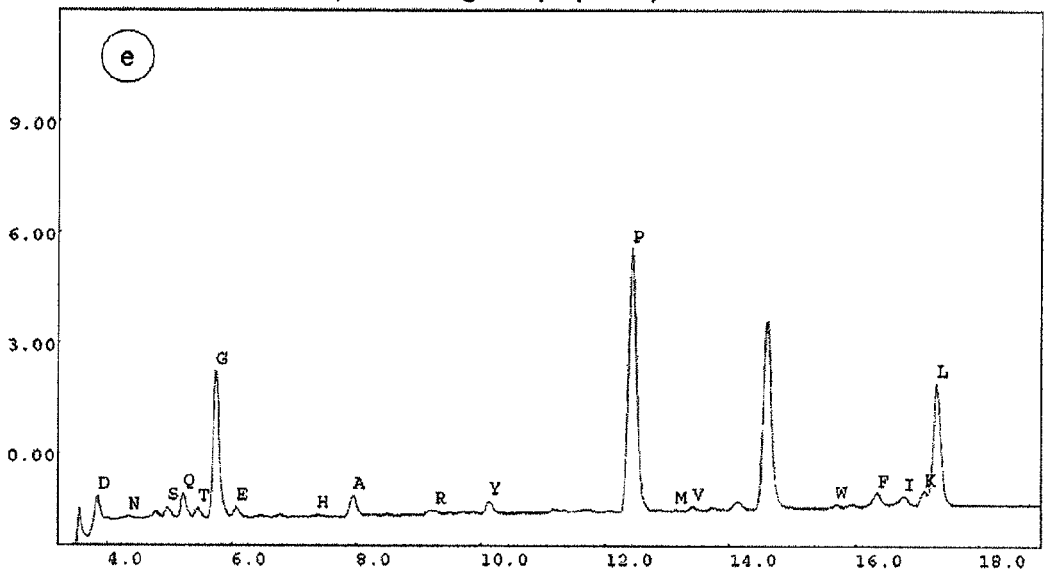
Figure 7:
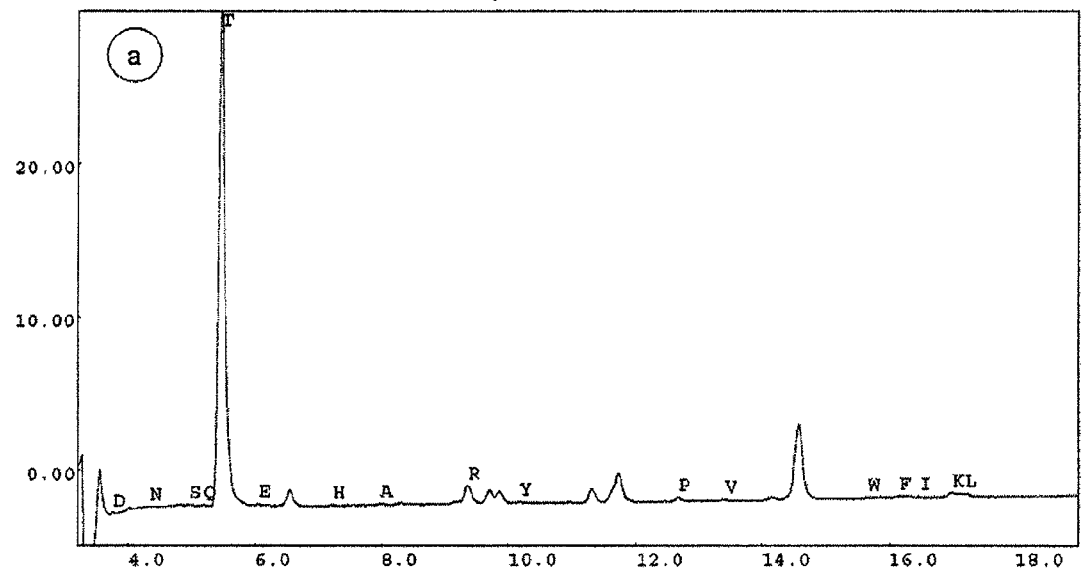
FIG. 7 shows the chromatogram of amino terminal amino acid sequencing (Edman degradation) of GRANOCYTE.
Figure 7:
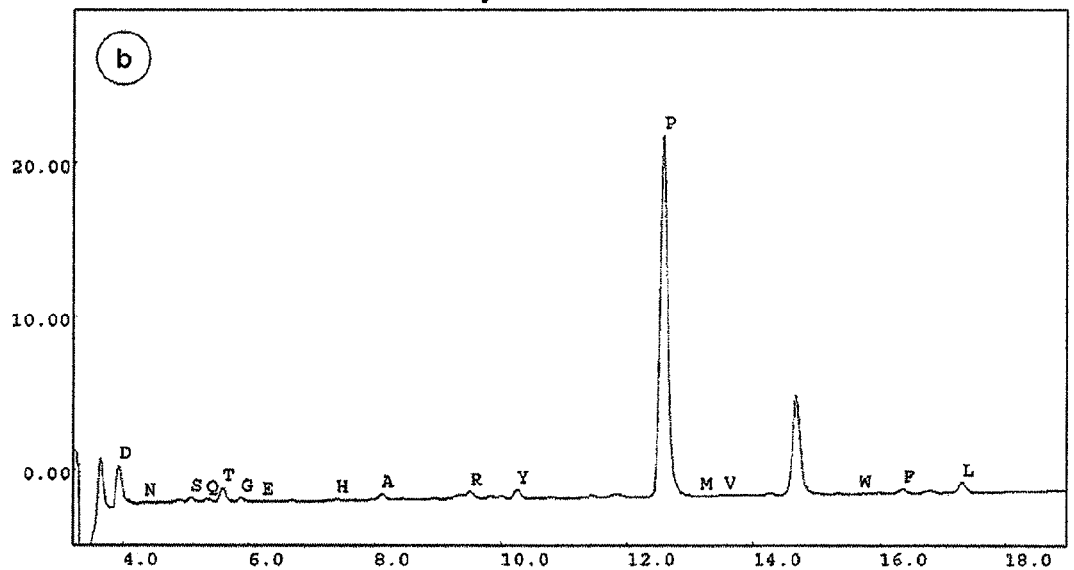
Figure 7:
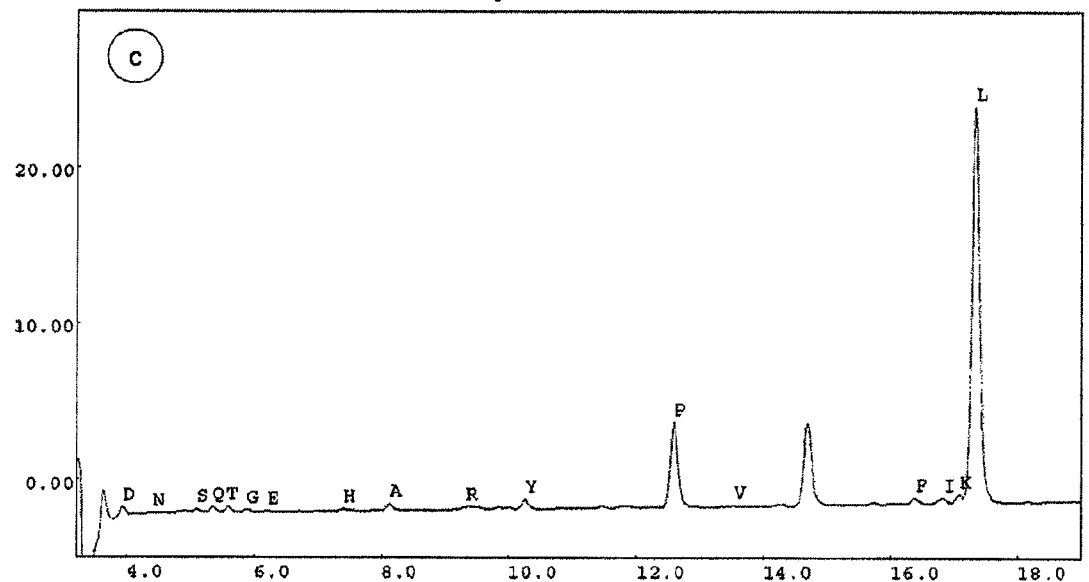
Figure 7:
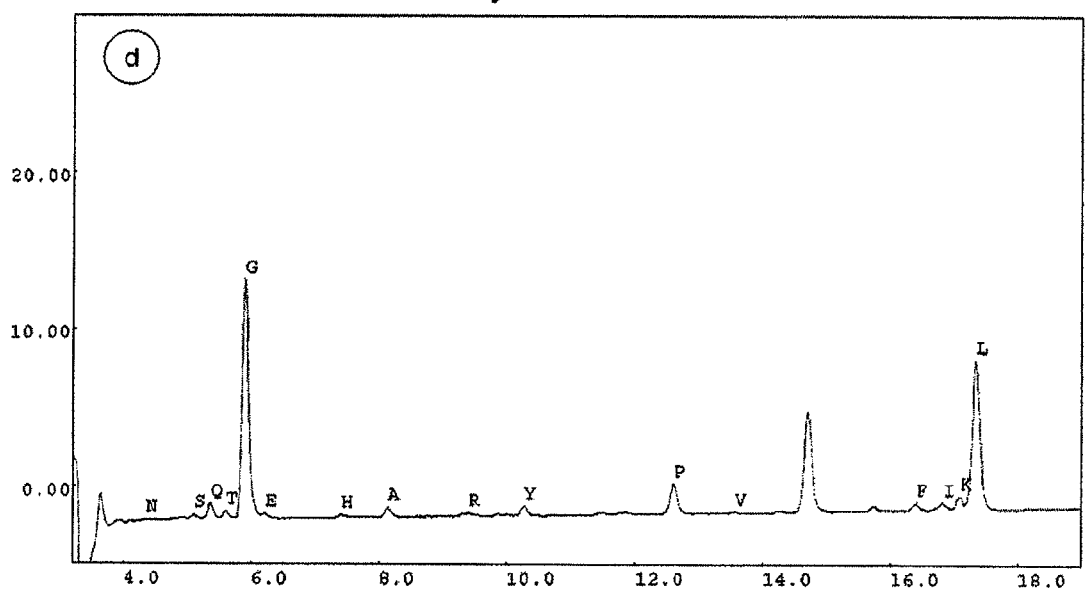
Figure 7:
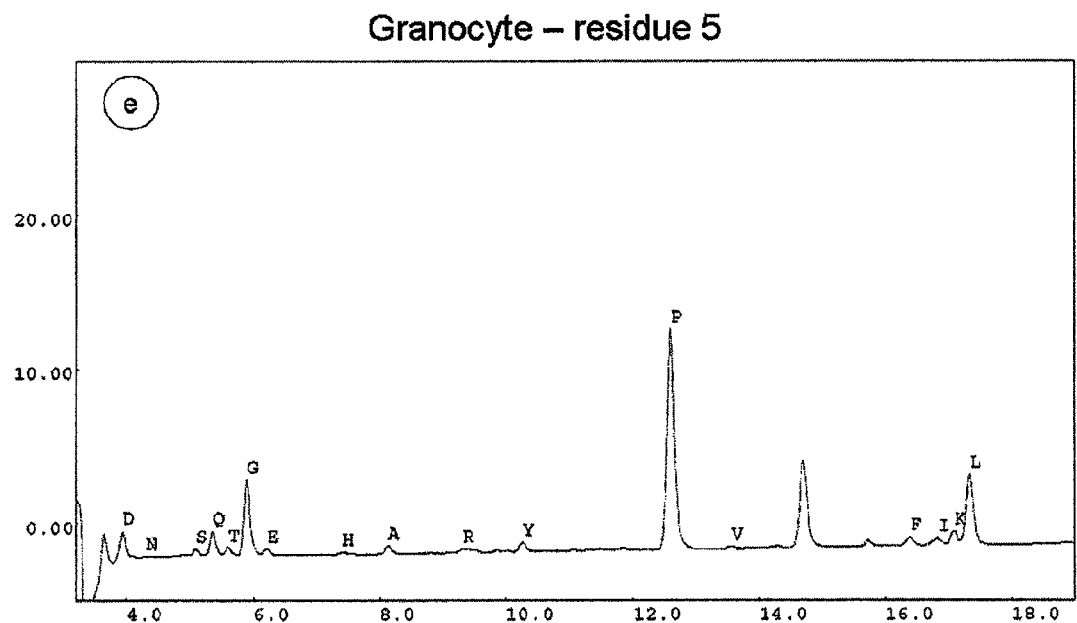
Figure 8:
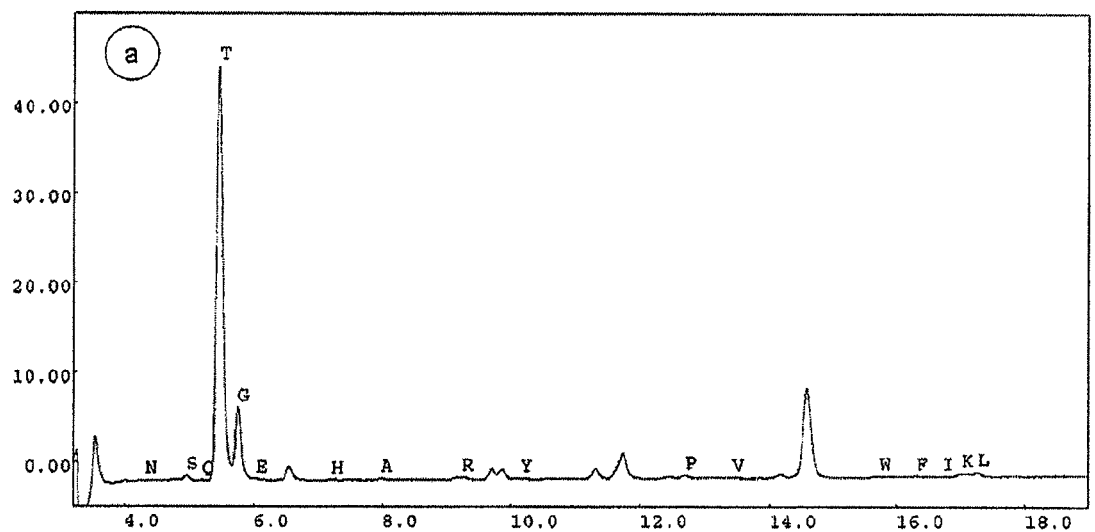
FIG. 8 shows the chromatogram of amino terminal amino acid sequencing (Edman degradation) of human, wild-type G-CSF with wild-type signal peptide.
Figure 8:
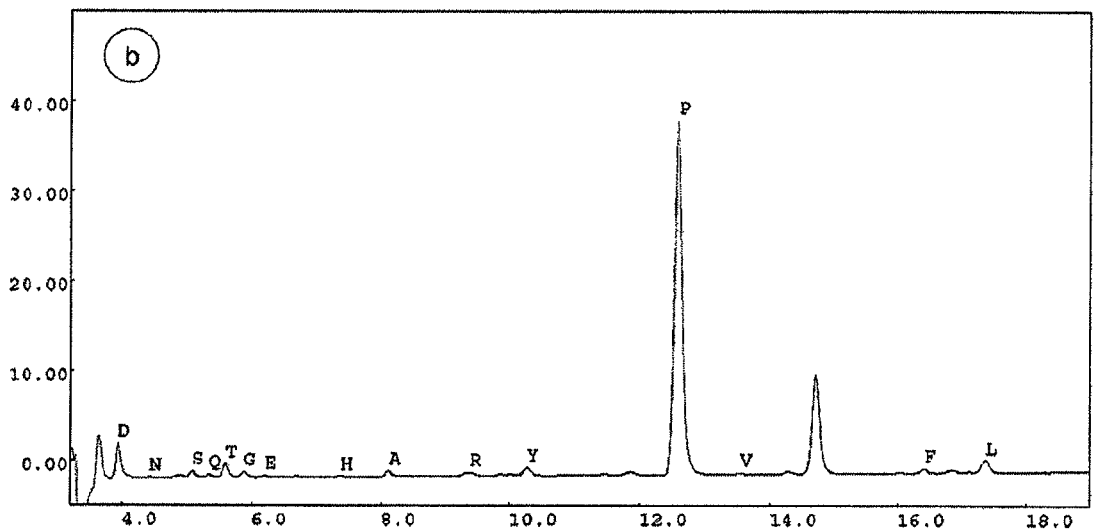
Figure 8:
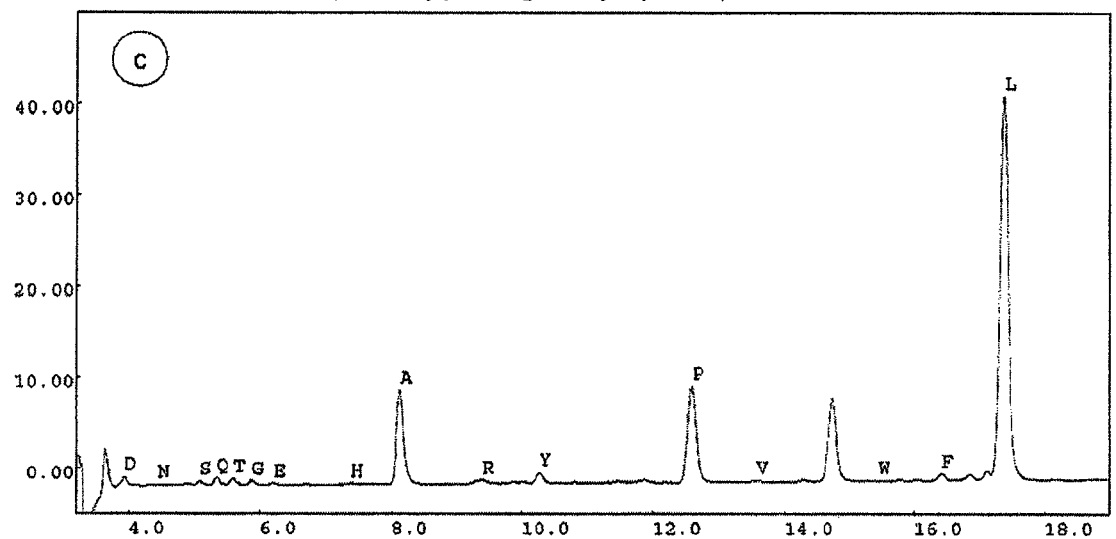
Figure 8:
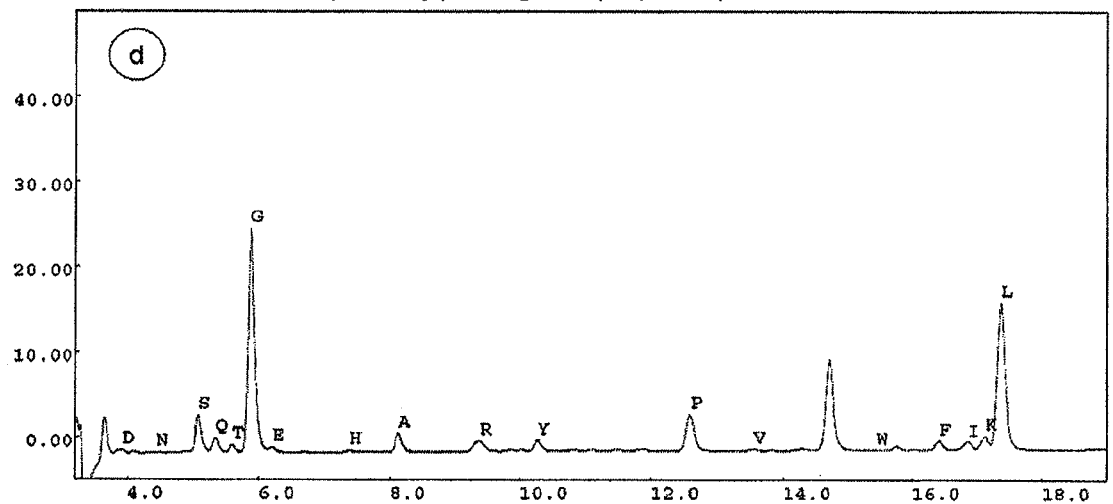
Figure 8:
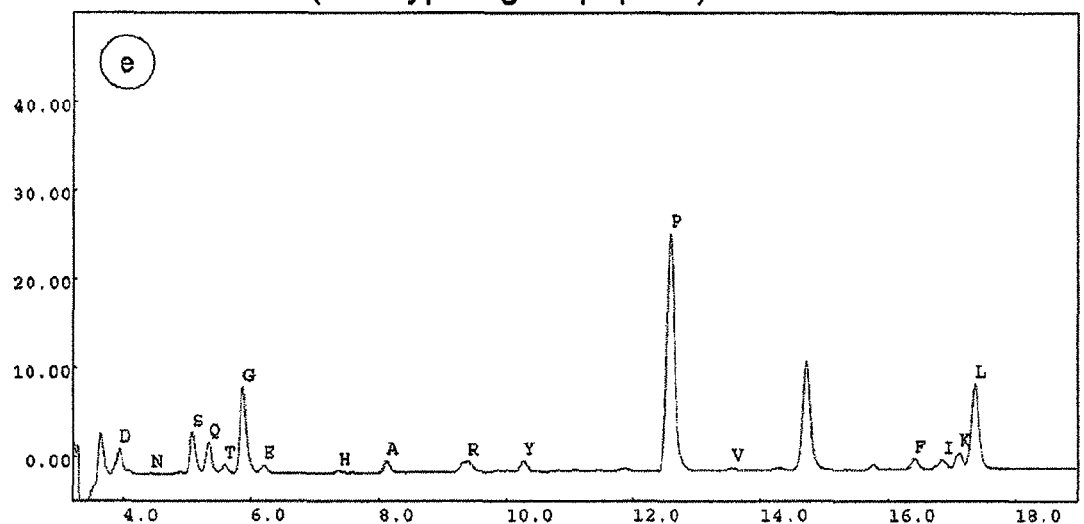

The amino terminal sequences of wild-type G-CSF, the commercial product GRANOCYTE (Chugai patent CA1341389, G-CSF produced in CHO cells), SP9 G-CSF and SP10 G-CSF were determined by Edman degradation (TopLab, Martinsried, Germany). Surprisingly, the data of the two expression products SP9 G-CSF and SP10 G-CSF revealed only the correct N-teminus without any truncation (FIG. 5 and FIG. 6). The same was observed for GRANOCYTE (FIG. 7). In contrast, the truncation was found for G-CSF with wild-type signal peptide (FIG. 8)—and for several other designed constructs, although only one cleavage site is predicted by SignalP or TargetP in silico (not shown).

EXAMPLE 7

The activity of SP9 G-CSF and SP10 G-CSF was measured in a cell proliferation assay and compared to GRANOCYTE. The cell proliferating activity of SP9 G-CSF and SP10 G-CSF was superior to that of Granocyte.

EXAMPLE 8

Glycosylation of SP9 G-CSF and SP10 G-CSF was determined by MALDI TOF peptide mass fingerprint analysis after GluC digestion. The reflector spectrum did not show any difference of SP9 G-CSF or SP10 G-CSF to wild-type G-CSF produced in HEK293F cells.

EXAMPLE 9

Evaluation of Clones Resulting from a Stable Transfection with Expression Vector Coding for SP9 G-CSF HEK293F cells were stably transfected with the expression vector coding for SP9 G-CSF. Homogeneous clones were isolated after stabilisation of the transfection. Supernatants of selected clones were analysed for different fermentation scales. For this G-CSF was purified to high purity from the collected supernatants and evaluated regarding their amino terminal sequence, glycosylation pattern and activity.

It was observed that, although the N-terminal truncation by 3 amino acids was not observable for the SP9 G-CSF resulting supernatant analysed from a transient transfection pool, the 3 amino acid truncation could not be suppressed fully for some clones. This effect was clone dependant and furthermore dependant on the cultivation scale and the cultivation conditions.

Figure 9:
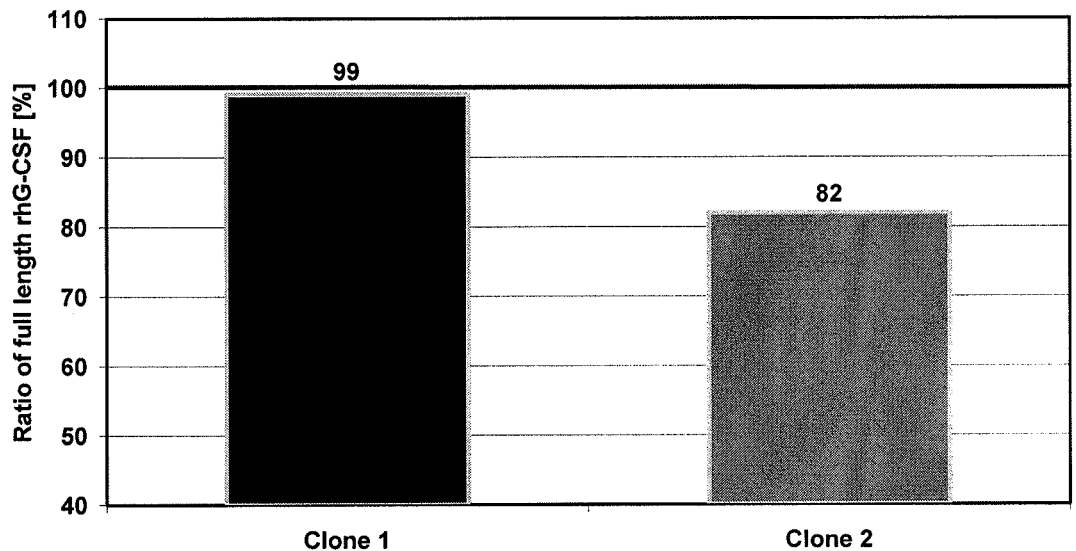
FIG. 9 shows the comparison of ratio of full length G-CSF for 2 exemplary clones resulting from the clone isolation of a stable transfection with G-CSF SP9. The residual—non full length fraction mainly comprises the N-terminally truncated G-CSF by 3 amino acids. The line at 99% full length G-CSF ratio correlates with the N-terminal truncation of ≦1%, which is the lower detection limit of the analysis.

The clone dependency (FIG. 9) suggested that the modification of the G-CSF signal peptide sequence resulting in the SP9 G-CSF vector supports the correct cleavage of the signal peptide to a major extent; nevertheless a 100% correct cleavage is still influenced by the clone specific metabolism.

The main approach to influence clone specific metabolism is the application of optimised culturing conditions.

Figure 10:
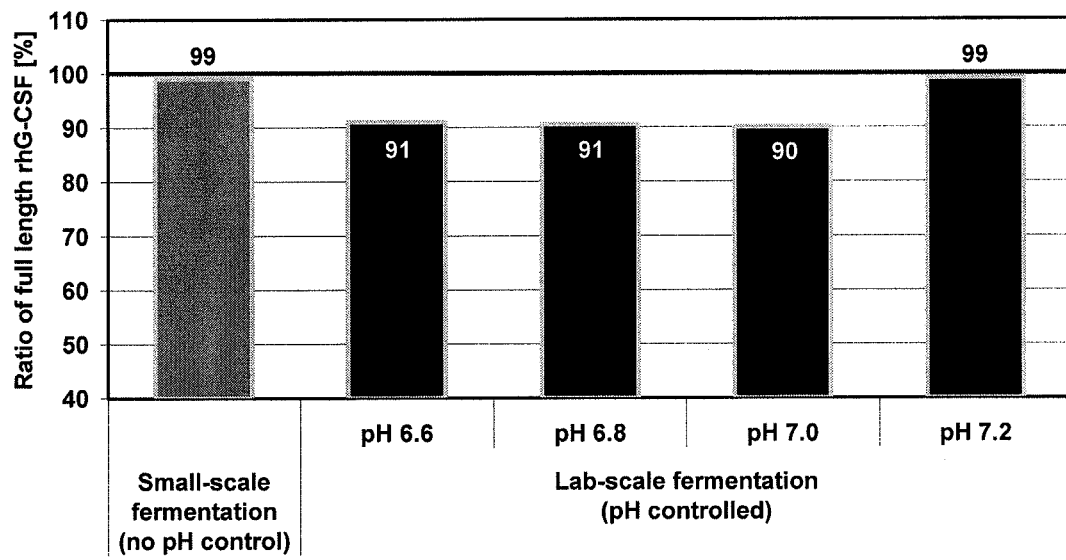
FIG. 10 shows the comparison of ratio of full length G-CSF on example of clone 1 for different cultivation pH in stirred-tank reactor cultivations. Clone 1 results from the clone isolation of a stable transfection with G-CSF SP9 vector. The residual—non full length fraction mainly comprises the N-terminally truncated G-CSF by 3 amino acids. The ratio of full length G-CSF of the reference cultivation for clone 1 in shaking flasks (without pH control) is depicted in the first bar in grey. The line at 99% full length G-CSF ratio correlates with the N-terminal truncation of ≦1%, which is the lower detection limit of the analysis.
Figure 11:
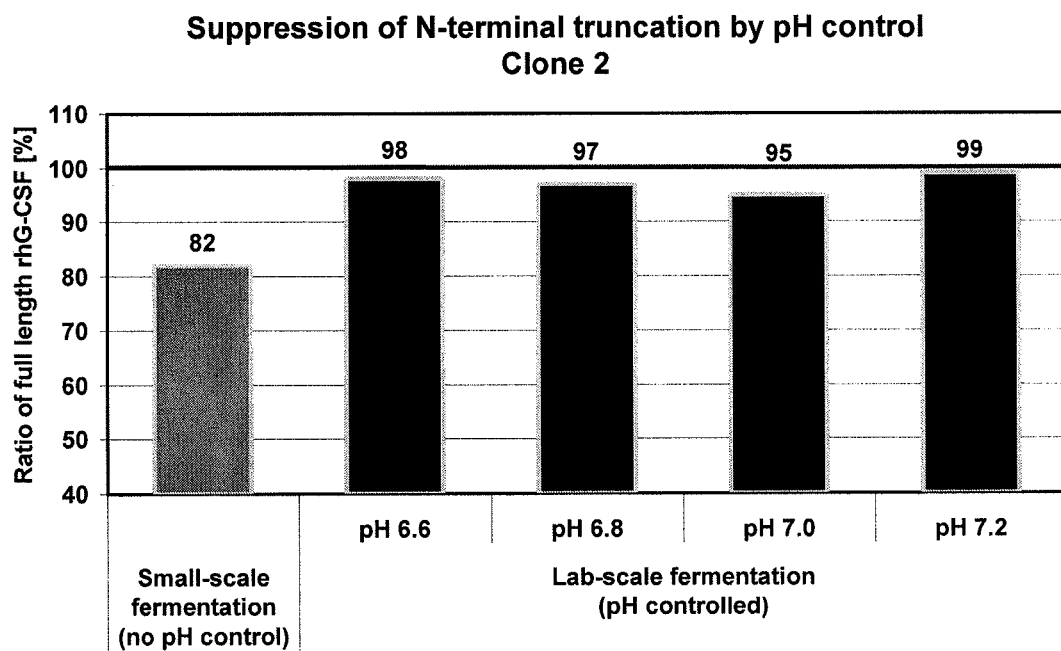
FIG. 11 shows the comparison of ratio of full length G-CSF on example of clone 2 for different cultivation pH in stirred-tank reactor cultivations. Clone 2 results from the clone isolation of a stable transfection with G-CSF SP9 vector. The residual—non full length fraction mainly comprises the N-terminally truncated G-CSF by 3 amino acids. The ratio of full length G-CSF of the reference cultivation for clone 2 in shaking flasks (without pH control) is depicted in the first bar in grey. The line at 99% full length G-CSF ratio correlates with the N-terminal truncation of 1%, which is the lower detection limit of the analysis.

The influence of cultivation pH on the correct cleavage of the signal peptide sequence of G-CSF was evaluated for 2 exemplary clones. Both clones were cultivated in lab-scale stirred tank reactors, each with defined pH values of 6.6; 6.8; 7.0 and 7.2. The G-CSF containing supernatants were purified to high purity and evaluated regarding their amino terminal sequence (FIG. 10 and FIG. 11). For both exemplary clones it was observed that a correct processing of the signal peptide sequence, which results in a full length G-CSF ratio of >99%, can be achieved by controlling the pH of the cell cultivation of the G-CSF clones to pH 7.2. The value of >99% corresponds to the lower detection limit of the sequencing method of 1%.

EXAMPLE 10

Figure 12:
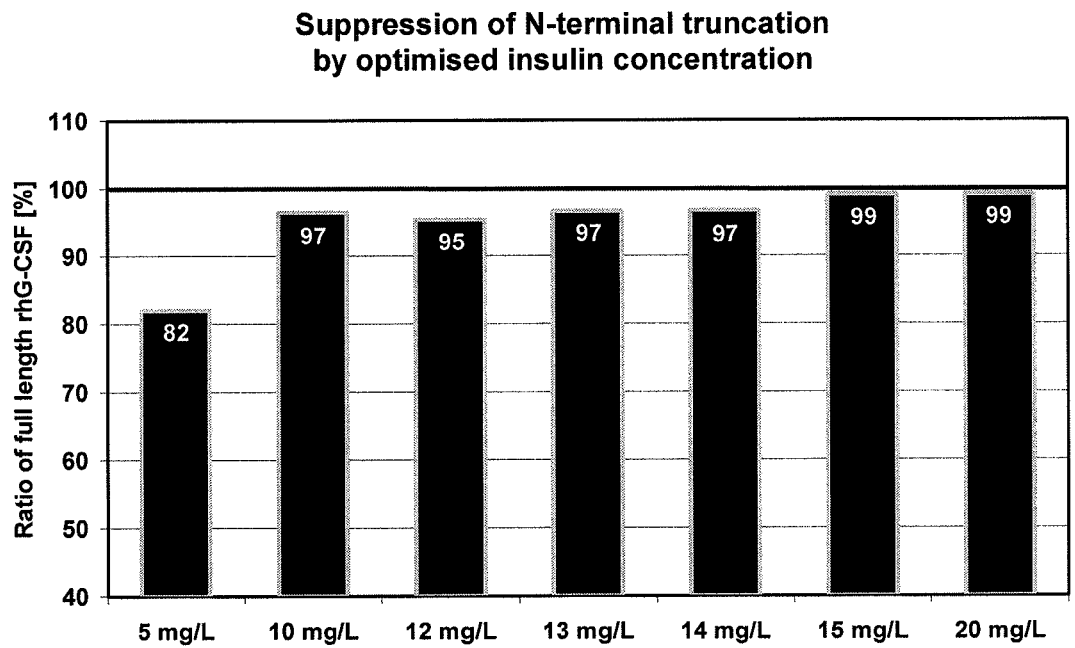
FIG. 12 shows the comparison of ratio of full length G-CSF on example of clone 2 for different insulin concentrations in the cultivation medium. Clone 2 results from the clone isolation of a stable transfection with G-CSF SP9 vector. The residual—non full length fraction mainly comprises the N-terminally truncated G-CSF by 3 amino acids. The line at 99% full length G-CSF ratio correlates with the N-terminal truncation of ≦1%, which is the lower detection limit of the analysis.

Shaking flask cultivations without pH control and with variation of the insulin concentration in the cultivation media were performed on the example of one clone. The insulin concentrations were varied in a range between 5 mg/L insulin to 20 mg/L insulin. The G-CSF containing supernatants were purified to high purity and evaluated regarding their amino terminal sequence (FIG. 12). On the example of the evaluated clone it was observable that the optimisation of the insulin concentration in the cultivation medium to a range between 15 to 20 mg/L insulin for the case of non-pH controlled cultivation conditions resulted in a correct processing of the signal peptide sequence.

Figure 13:
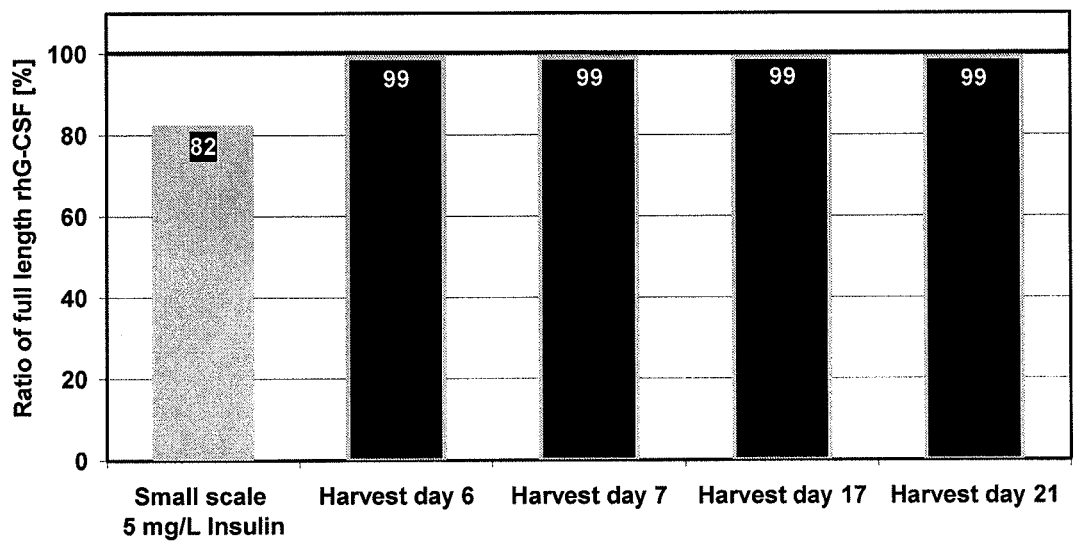
FIG. 13 shows the comparison of ratio of full length G-CSF for different harvest days on example of clone 2 cultivated in a large-scale high cell density mode, with application of 15 mg/L insulin to the cultivation medium, without application of a pH control. Clone 2 results from the clone isolation of a stable transfection with G-CSF SP9 vector. The residual—non full length fraction mainly comprises the N-terminally truncated G-CSF by 3 amino acids. The line at 99% full length G-CSF ratio correlates with the N-terminal truncation of ≦1%, which is the lower detection limit of the analysis.

A large-scale high cell density cultivation using the perfusion mode for medium supply was performed on the example of one clone. The pH of the cultivation was not controlled and varies in a range of 6.8 to 7.2 during the cultivation. The insulin concentration in the cultivation medium was adjusted to the optimised concentration of 15 mg/L insulin. G-CSF containing supernatants from 4 selected cultivation time points on cultivation day 6, 7, 17 and 21 were purified to high purity and evaluated regarding their amino terminal sequence (FIG. 13). A correct processing of the signal peptide sequence, resulting in >99% full length G-CSF, was achieved for all analysed supernatants, independent from cell density and G-CSF productivity. The application of an optimised insulin concentration of 15 mg/L is thus effective for avoidance of N-terminal truncation in large-scale high cell density cultivations.

The invention claimed is:

1. An isolated G-CSF precursor comprising a signal peptide and a G-CSF peptide, wherein the signal peptide has the sequence of the human wild-type signal peptide of the human G-CSF/b molecule but has at least one mutation selected from the group consisting of: deletion of Glu29, insertion of Glu26, substitution Lys11Leu, substitution His21 Phe, and substitution Gln28Leu.

2. The isolated G-CSF precursor of claim 1, having at least two, or at least three, or at least four or five of the mutations of claim 1.

3. The isolated G-CSF precursor of claim 1, having up to 3 additional mutations in the signal peptide selected from insertion, deletion and substitution.

4. An isolated polynucleotide coding for the G-CSF precursor of claim 1.

5. An isolated polynucleotide completely complementary to the polynucleotide of claim 4.

6. A vector comprising the polynucleotide of claim 4.

7. A transfected cell comprising the polynucleotide of claim 4 or a vector comprising the polynucleotide of claim 4.

8. The transfected cell of claim 7, wherein the cell is a eukaryotic cell.

9. The transfected cell of claim 8, wherein the eukaryotic cell is a human cell.

10. The transfected cell of claim 8, wherein the eukaryotic cell is an HEK293 cell.

11. The transfected cell of claim 8, wherein the eukaryotic cell is an HEK293F cell.

12. The transfected cell of claim 7, wherein the transfection is transient.

13. The transfected cell of claim 7, wherein the transfection is stable.

14. A method for expressing a G-CSF precursor comprising the steps of culturing the transfected cell of claim 7 in a suitable culture medium and isolating the G-CSF precursor from the culture medium.

15. The method of claim 14, wherein culturing is at a pH within the range of 6.8 to 7.5.

16. The method of claim 14, wherein culturing is in the presence of insulin in the range of 5 to 25 mg/ml.

17. The method of claim 14, wherein the culture medium is serum-free.

18. The method of claim 14, wherein culturing is at a pH within the range of 7.1 to 7.3.

19. The method of claim 14, wherein culturing is in the presence of insulin in the range of 15 to 25 mg/ml.

20. The method of claim 14, wherein culturing is in the presence of insulin in the range of 15 to 20 mg/ml.

* * * * *

UNITED STATES PATENT AND TRADEMARK OFFICE
CERTIFICATE OF CORRECTION

PATENT NO. : 8,436,142 B2
APPLICATION NO. : 13/122487
DATED : May 7, 2013
INVENTOR(S) : Schroeder et al.

Page 1 of 1

It is certified that error appears in the above-identified patent and that said Letters Patent is hereby corrected as shown below:

On the Title page item [73] Assignee should read

<u>Octapharma Biopharmaceuticals GmbH, Martinsried, (DE)</u>

Signed and Sealed this
Tenth Day of September, 2013

Teresa Stanek Rea
*Acting Director of the United States Patent and Trademark Office*